US011016089B2

(12) United States Patent
Biris et al.

(10) Patent No.: US 11,016,089 B2
(45) Date of Patent: May 25, 2021

(54) NANOCOMPOSITES AND NANOAGENTS FOR DETECTION AND TREATMENT OF A TARGET OF INTEREST AND METHODS OF MAKING AND USING SAME

(71) Applicant: BOARD OF TRUSTEES OF THE UNIVERSITY OF ARKANSAS, Little Rock, AR (US)

(72) Inventors: Alexandru S. Biris, Little Rock, AR (US); Zeid A. Nima, Little Rock, AR (US)

(73) Assignee: BOARD OF TRUSTEES OF THE UNIVERSITY OF ARKANSAS, Little Rock, AR (US)

(*) Notice: Subject to any disclaimer, the term of this patent is extended or adjusted under 35 U.S.C. 154(b) by 107 days.

(21) Appl. No.: 15/487,683

(22) Filed: Apr. 14, 2017

(65) Prior Publication Data

US 2017/0219575 A1 Aug. 3, 2017

Related U.S. Application Data

(63) Continuation-in-part of application No. 14/921,927, filed on Oct. 23, 2015, now Pat. No. 9,700,573, and
(Continued)

(51) Int. Cl.
*G01N 33/553* (2006.01)
*G01N 33/574* (2006.01)
(Continued)

(52) U.S. Cl.
CPC ......... *G01N 33/553* (2013.01); *A61K 31/337* (2013.01); *A61K 31/704* (2013.01);
(Continued)

(58) Field of Classification Search
None
See application file for complete search history.

(56) References Cited

U.S. PATENT DOCUMENTS 10,688,556 B2 * 6/2020 Matsui ................. B22F 1/0062
2006/0073336 A1 4/2006 Zhang et al.
(Continued)

FOREIGN PATENT DOCUMENTS

WO 2005062741 A2 7/2005
WO 2008122035 A1 10/2008

OTHER PUBLICATIONS

Skadtchenko et al. "Surface-enhance Raman scattering of p-nitrothiophenol Molecular vibrations of its silver salt and the surface complex formed on silver islands and colloids" Spectrochimica Acta, Part A, 57 (2001) pp. 1009-1016. (Year: 2001).*
(Continued)

*Primary Examiner* — Katherine Peebles
*Assistant Examiner* — Casey S Hagopian
(74) *Attorney, Agent, or Firm* — Locke Lord LLP; Tim Tingkang Xia, Esq.

(57) ABSTRACT

A nanocomposite for detection and treatment of a target of interest including tumor cells or pathogens includes at least one nanostructure, each nanostructure having a core and a shell surrounding the core; a reporter assembled on the shell of each nanostructure; and a layer of a treating agent and a targeting agent conjugated to the reporter. In use, the nanocomposite targets to the target of interest according to the targeting agent and releases the treating agent and the nanostructure therein for therapeutic treatment of the target of interest, and the target of interest transmits at least one signature responsive to the reporter for detection of the target of interest.

17 Claims, 8 Drawing Sheets
(7 of 8 Drawing Sheet(s) Filed in Color)

Related U.S. Application Data a continuation-in-part of application No. 14/683,929, filed on Apr. 10, 2015, now Pat. No. 9,810,687, and a continuation-in-part of application No. 14/683,978, filed on Apr. 10, 2015, now Pat. No. 9,675,078, and a continuation-in-part of application No. 14/513,744, filed on Oct. 14, 2014, now Pat. No. 9,784,737, and a continuation-in-part of application No. 14/181,981, filed on Feb. 17, 2014, now abandoned.

(60) Provisional application No. 62/322,489, filed on Apr. 14, 2016.

(51) Int. Cl.

| | |
|---|---|
| *A61K 31/704* | (2006.01) |
| *A61K 49/00* | (2006.01) |
| *A61K 47/68* | (2017.01) |
| *H01F 1/00* | (2006.01) |
| *A61K 47/69* | (2017.01) |
| *A61K 9/00* | (2006.01) |
| *B82Y 15/00* | (2011.01) |
| *B82Y 30/00* | (2011.01) |
| *B82Y 5/00* | (2011.01) |
| *G01N 33/531* | (2006.01) |
| *A61K 31/337* | (2006.01) |
| *A61K 41/00* | (2020.01) |
| *B01J 13/22* | (2006.01) |
| *B32B 15/02* | (2006.01) |
| *B01J 13/06* | (2006.01) |
| *B01J 13/20* | (2006.01) |
| *B01J 13/02* | (2006.01) |
| *B82Y 40/00* | (2011.01) |
| *A61N 1/40* | (2006.01) |

(52) U.S. Cl.
CPC ...... *A61K 41/0052* (2013.01); *A61K 47/6849* (2017.08); *A61K 47/6923* (2017.08); *A61K 49/0065* (2013.01); *B01J 13/02* (2013.01); *B01J 13/06* (2013.01); *B01J 13/20* (2013.01); *B01J 13/22* (2013.01); *B32B 15/02* (2013.01); *G01N 33/531* (2013.01); *G01N 33/57492* (2013.01); *H01F 1/0054* (2013.01); *A61K 9/0092* (2013.01); *A61N 1/406* (2013.01); *B82Y 5/00* (2013.01); *B82Y 15/00* (2013.01); *B82Y 30/00* (2013.01); *B82Y 40/00* (2013.01)

(56) References Cited

U.S. PATENT DOCUMENTS

| | | | |
|---|---|---|---|
| 2011/0165077 A1* | 7/2011 | Qian | A61K 49/0089 424/9.1 |
| 2012/0014878 A1* | 1/2012 | Culha | C07H 21/00 424/9.1 |
| 2014/0178475 A1* | 6/2014 | Figueiredo | A61K 9/5153 424/489 |
| 2016/0077090 A1* | 3/2016 | Biris | G01N 33/54346 435/5 |

OTHER PUBLICATIONS

Okuno et al. "Uniform and controllable preparation of Au—Ag core-shell nanorods using anisotropic silver shell formation of gold nanorods" Nanoscale, 2010, 2, pp. 1489-1493. (Year: 2010).*

Huang et al. "Surface-enhance Raman spectroscopic study of p-aminothiophenol" Phys. Chem. Chem. Phys., 2012, 14, 8485-8497. (Year: 2012).*

Nima et al. "Circulating tumor cell identification by functionalized silver-gold nanorods with multicolor, super-enhanced SERS and photothermal resonances", Scientific Reports, 4, 4752, May 2014, pp. 1-8. (Year: 2014).*

Fales, et al., "Development of Hybrid Silver-Coated Gold Nanostars for Nonaggregated Surface-Enhanced Raman Scattering", The Journal of Physical Chemistry C Nanomater Interfaces, 2014, pp. 3708-3715, vol. 118(7).

Huh et al., "Surface enhanced Raman spectroscopy and its application to molecular and cellular analysis". Microfluid Nanofluid, 2009, pp. 285.297, vol. 6.

Korean Intellectual Property Office, "International Search Report for PCT/US2017/027613", KR, Aug. 8, 2017.

Cho, Kwangjae et al., "Therapeutic Nanoparticles for Drug Delivery in Cancer", Clinical Cancer Research, American Association for Cancer Research, vol. No. 14, Issue No. 5, pp. 1310-1316, Mar. 1, 2008.

Saeed, LM et al., "Single-walled carbon nanotube and graphene nanodelivery of gambogic acid increases its cytotoxicity in breast and pancreatic cancer cells", Journal of Applied Toxicology, vol. No. 34, Issue No. 11, pp. 1188-1199, Received: Jan. 24, 2014.

Mahmood Meena et al., "Calcium-channel blocking and nanoparticles-based drug delivery for treatment of drug-resistant human cancers", Therapeutic Delivery, Future Science Group, vol. No. 5, Issue No. 7, pp. 763-780, 2014.

Nima, ZA et al., "Circulating tumor cell identification by functionalized silver-gold nanorods with multicolor, super-enhanced SERS and photothermal resonances", Nature Scientific Reports, vol. 4:4752, pp. 1-8, Received: Jan. 10, 2014.

Nima, ZA et al., "Applications of surface-enhanced Raman scattering in advanced bio-medical technologies and diagnostics", Drug Metabolism Reviews, vol. No. 46, Issue No. 2, pp. 155-175, Received: Oct. 3, 2013.

Zavaleta, CL et al., "Multiplexed imaging of surface enhanced Raman scattering nanotags in living mice using noninvasive Raman spectroscopy", vol. No. 106, Issue No. 32, pp. 13511-13516, Aug. 11, 2009.

Nikoobakht, Babak et al., "Surface-enhanced Raman scattering of molecules adsorbed on gold nanorods: off-surface plasmon resonance condition", Chemical Physics Letters, vol. No. 366, Issues 1-2, pp. 17-23, 2002.

Becker, Jan et al., "Plasmonic Focusing Reduces Ensemble Linewidth of Silver-Coated Gold Nanorods", Nano Letters, vol. No. 8, Issue No. 6, pp. 1719-1723, Published on Web: May 3, 2008.

Liu, Mingzhao et al., "Synthesis and Optical Characterization of Au/Ag Core/Shell Nanorods", Journal of Physical Chemistry B, vol. No. 108, Issue No. 19, pp. 5882-5888, Published on Web: Apr. 16, 2004.

Kulin, Simone et al., "Real-Time Measurement of Spontaneous Antigen-Antibody Dissociation", Biophysical Journal, vol. No. 83, Issue No. 4, pp. 1965-1973, Oct. 2002.

Nima, ZA et al., "Single-walled carbon nanotubes as specific targeting and Raman spectroscopic agents for detection and discrimination of single human breast cancer cells", Journal of Biomedical Optics, vol. No. 18, Issue No. 5, pp. 055003-1-055003-11, May 2013.

Nikoobakht, Babak et al., "Preparation and Growth Mechanism of Gold Nanorods (NRs) Using Seed-Mediated Growth Method", Chemistry of Materials, vol. No. 15, Issue No. 10, pp. 1957-1962, Published on Web: Apr. 17, 2003.

* cited by examiner

NANOCOMPOSITES AND NANOAGENTS FOR DETECTION AND TREATMENT OF A TARGET OF INTEREST AND METHODS OF MAKING AND USING SAME

CROSS-REFERENCE TO RELATED APPLICATIONS

This application claims priority to and the benefit of, pursuant to 35 U.S.C. §119(e), U.S. provisional patent application Ser. No. 62/322,489, filed Apr. 14, 2016, which is incorporated herein in its entirety by reference.

This application is also a continuation-in-part application of U.S. co-pending patent application Ser. No. 14/181,981, filed Feb. 17, 2014; Ser. No. 14/513,744, filed Oct. 14, 2014; Ser. No. 14/683,929, filed Apr. 10, 2015; Ser. No. 14/683,978, filed Apr. 10, 2015; and Ser. No. 14/921,927, filed Oct. 23, 2015, which are incorporated herein in their entireties by reference.

Some references, which may include patents, patent applications, and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [5] represents the fifth reference cited in the reference list, namely, Nima Z A, Biswas A, Bayer I S, Hardcastle F D, Perry D, Ghosh A, et al. Applications of surface-enhanced Raman scattering in advanced bio-medical technologies and diagnostics*. Drug Metabolism Reviews. 2014:1-21. doi: 10.3109/03602532.2013.873451.

STATEMENT AS TO RIGHTS UNDER FEDERALLY-SPONSORED RESEARCH

This invention was made with government support under grant number IIA-1457888 awarded by the National Science Foundation. The government has certain rights in the invention.

FIELD OF THE INVENTION

The invention relates generally to detections of cancer cells or pathogens, and more particularly to nanocomposites, methods of making the same, and applications of the same for multicolor surface enhanced Raman spectroscopy (SERS) detections and imaging of cancer cells or pathogens.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the present invention.

Various kinds of nanoparticles have been used as drug-delivery agents: polymers, liposomes, viruses, micelles, dendrimers [1], carbon nanotubes [2], graphene [2], and metallic nanoparticles [3]. However, most of these systems possess rather limited functionalities. A successful nano-sized system that is expected to be used in clinical applications related to cancer diagnosis and treatment, needs to have multifunctional/tunable characteristics that include the following: controllable surface chemistry/energy, stability in liquid environments against agglomeration and corrosion, lack of toxicity, ability to generate unique and intense signals that can be detected with high resolution in tissues, capability to be attached to various targeting agents (antibodies), capacity to carry/deliver drugs or biochemically-active molecules.

Therefore, a heretofore unaddressed need exists in the art to address the aforementioned deficiencies and inadequacies.

SUMMARY OF THE INVENTION

In certain aspects, this invention is based on using plasmonically active silver-decorated gold nanorods (AuNR/Ag) as specific targeting dual drug delivery system. Using coupling reactions, doxorubicin (D1) and anti-EpCAM (Ab1) and Docetaxel (D2) and anti-CD44 (Ab2) antibodies are covalently bound to thiolated polyethylene glycol-coated AuNR/Ag and then used as a vehicle to specifically trace and deliver lethal doses of chemotherapy. This nanorod based system with specific Raman spectroscopic properties could additionally provide unique and strong signals to enable their accurate detection inside cells and further confirm their strong interactions with them. The development of plasmonically active nanodrug concepts with unique signatures could represent a possible approach for the specific targeting and visualization of cells, as well as solid tumors, while delivering anti-cancer molecules for enhanced cancer treatment.

In certain aspects, the invention also relates to a method to deliver to single cancer cell micro- or macro-tumors, a multitude of drug delivery vehicles, each with a different antibody or targeting molecule and each with a different drug. The goal is to synergistically enhance the death rates of the cancer cells by the delivery of a multitude of drugs attached to nanovehicles connected to a multitude of targeting molecules. Additionally, the plasmonic nanorods, can be decorated with a multitude of Raman scattering molecules that can provide multiple signatures for their accurate determination and detection. This method is capable of detecting and quantifying each of the drugs from a multitude of drug cocktails that reach the cancer cells, micro or macro tumors.

In one aspect, the invention relates to a nanocomposite for detection and treatment of a target of interest, where the target of interest comprises tumor cells or pathogens. In one embodiment, the nanocomposite includes at least one nanostructure, each nanostructure having a core and a shell surrounding the core; a reporter assembled on the shell of each nanostructure; and a layer of a treating agent and a targeting agent conjugated to the reporter. In use, the nanocomposite targets to the target of interest according to the targeting agent and releases the treating agent and the nanostructure therein for therapeutic treatment of the target of interest, and the target of interest transmits at least one signature responsive to the reporter for detection of the target of interest.

In one embodiment, each core comprises a nanoparticle including a gold nanorod, and wherein the shell comprises a layer comprising silver nanoparticles.

In one embodiment, the reporter comprises 4-mercaptobenzoic acid (4MBA), p-aminothiophenol (PATP), p-nitrothiophenol (PNTP), 4-(methylsulfanyl)thiophenol (4MSTP), molecules with an unique Raman spectral signature, or a fluorescent agent.

In one embodiment, the at least one signature transmitted from the target of interest responsive to the reporter is detectable by at least one of surface enhanced Raman spectroscopy (SERS), magnetic resonance imaging (MRI), x-ray radiography, computed tomography (CT), and infrared spectroscopy (IR).

In one embodiment, he treating agent comprises a drug, a growth factor, a protein, or other biologically active molecules.

In one embodiment, the targeting agent comprises anti-epithelial cell adhesion molecule antibody (anti-EpCAM), anti-CD44 antibody, anti-insulin-like growth factor 1 receptor antibody (anti-IGF-1R), anti-Keratin 18 antibody, or one or more antibodies specific to the target of interest.

In one embodiment, the nanocomposite further includes a pegylated layer formed between the reporter and the layer of the drug and the targeting agent, or formed between the shell and the reporter.

In one embodiment, the pegylated layer comprises at least one of thiolated polyethylene glycol (HS-PEG), thiolated polyethylene glycol acid (HS-PEG-COOH) and HS-PEG-NHx.

In one embodiment, the treating agent and the targeting agent are conjugated to the pegylated layer through a carboxylic group of the HS-PEG-COOH or amine group of the HS-PEG-NHx.

In another aspect, the invention relates to a method for detection and treatment of a target of interest, where the target of interest comprises tumor cells or pathogens. In one embodiment, the method includes administering to the target of interest an effective amount of the above nanocomposite, so that the nanocomposite targets to the target of interest according to the targeting agent and releases the treating agent and the nanostructure therein for therapeutic treatment of the target of interest; and measuring the at least one signature transmitted from the target of interest responsive to the reporter to detect the target of interest according to the measured signature.

In yet another aspect, the invention relates to a nanoagent for detections and treatments of multiple targets of interest, where each target of interest comprises a respective type of tumor cells or pathogens. In one embodiment, the nanoagent comprises multiple types of nanocomposites. Each type of nanocomposites includes at least one nanostructure, each nanostructure having a core and a shell surrounding the core; a respective reporter assembled on the shell of each nanostructure; and a layer of a respective treating agent and a respective targeting agent conjugated to the respective reporter. In use, each type of nanocomposite targets to a respective target of interest according to the respective targeting agent and releases the respective treating agent and the nanostructure therein for therapeutic treatment of the respective target of interest, and the respective target of interest transmits at least one signature responsive to the respective reporter for detection of the respective target of interest.

In one embodiment, each core comprises a nanoparticle including a gold nanorod, and wherein the shell comprises a layer comprising silver nanoparticles.

In one embodiment, the respective reporter comprises 4-mercaptobenzoic acid (4MBA), p-aminothiophenol (PATP), p-nitrothiophenol (PNTP), 4-(methylsulfanyl)thiophenol (4MSTP), molecules with an unique Raman spectral signature, or a fluorescent agent.

In one embodiment, the at least one signature transmitted from the respective target of interest responsive to the respective reporter is detectable by at least one of surface enhanced Raman spectroscopy (SERS), magnetic resonance imaging (MRI), x-ray radiography, computed tomography (CT), and infrared spectroscopy (IR).

In one embodiment, the respective treating agent comprises a drug, a growth factor, a protein, or other biologically active molecules.

In one embodiment, the respective targeting agent comprises anti-epithelial cell adhesion molecule antibody (anti-EpCAM), anti-CD44 antibody, anti-insulin-like growth factor 1 receptor antibody (anti-IGF-1R), anti-Keratin 18 antibody, or one or more antibodies specific to the target of interest.

In one embodiment, each type of nanocomposites further comprises a pegylated layer formed between the respective reporter and the layer of the respective drug and the respective targeting agent, or formed between the shell and the respective reporter.

In one embodiment, the pegylated layer comprises at least one of thiolated polyethylene glycol (HS-PEG), thiolated polyethylene glycol acid (HS-PEG-COOH) and HS-PEG-NHx.

In one embodiment, the respective treating agent and the respective targeting agent are conjugated to the pegylated layer through a carboxylic group of the HS-PEG-COOH or amine group of the HS-PEG-NHx.

In a further aspect, the invention relates to a method for detections and treatments of multiple targets of interest, where each target of interest comprises a respective type of tumor cells or pathogens. In one embodiment, the method comprises administering to the multiple targets of interest an effective amount of the above disclosed nanoagent, so that each type of nanocomposite targets to a respective target of interest according to the respective targeting agent and releases the respective treating agent and the nanostructure therein for therapeutic treatment of the respective target of interest; and measuring the at least one signature transmitted from each target of interest responsive to the respective reporter to detect the respective target of interest according to the measured signature.

In one aspect, the invention relates to a method of making a nanocomposite for detection and treatment of a target of interest, where the target of interest comprises tumor cells or pathogens. In one embodiment, the method comprises forming at least one nanostructure, each nanostructure having a core and a shell surrounding the core; assembling a reporter on the shell of each nanostructure, wherein the reporter is adapted for respectively transmitting at least one signature from the target of interest; and conjugating a layer of a treating agent and a targeting agent to the reporter, wherein the treating agent is adapted for treating the target of interest, and the targeting agent is adapted for targeting the nanocomposite to the target of interest.

In one embodiment, each core comprises a nanoparticle including a gold nanorod, and wherein the shell comprises a layer comprising silver nanoparticles.

In one embodiment, the step of assembling the reporter comprises dispersing the at least one nanostructure in distilled water to form a first mixture; dissolving the reporter in ethanol to form a reporter solution; adding the reporter solution to the first mixture and stirring to form a second mixture; and centrifuging the second mixture to form a first precipitate comprising the at least one nanostructure assembled with the reporter. In one embodiment, the reporter comprises 4-mercaptobenzoic acid (4MBA), p-aminothiophenol (PATP), p-nitrothiophenol (PNTP), 4-(methylsulfanyl)thiophenol (4MSTP), molecules with an unique Raman spectral signature, or a fluorescent agent.

In one embodiment, the method further comprises coating a thiolated PEG layer on the assembled reporter, comprising: dispersing the first precipitate in a thiolated polyethylene glycol acid (HS-PEG-COOH) solution and vigorously stirring to form a third mixture; adding thiolated polyethylene glycol (HS-PEG) to the third mixture and keeping it at a temperature for a period of time to form a fourth mixture; and centrifuging the fourth mixture to form a second precipitate, wherein the second precipitate comprises the nanostructure assembled with the reporter coated with the thiolated PEG layer.

In one embodiment, the step of conjugating the layer of the treating agent and the targeting agent to the reporter comprises suspending the second precipitate in a PBS buffer by sonicating to form a suspending mixture; adding N-hydroxysuccinimide (NETS) and 1N-ethyl-N'-(3-dimethylaminopropyl) carbodiimide hydrochloride (EDC) to the suspending mixture and stirring to form a fifth mixture; washing the fifth mixture by centrifuging to obtain a third precipitate; dispensing the third precipitate in the PBS buffer to form a sixth mixture; adding the treating agent and/or the targeting agent to the sixth mixture and mixing thoroughly to form a seventh mixture; and stirring the seventh mixture at a temperature to form the nanocomposite.

In one embodiment, the treating agent comprises a drug, a growth factor, a protein, or other biologically active molecules.

In one embodiment, the targeting agent comprises anti-epithelial cell adhesion molecule antibody (anti-EpCAM), anti-CD44 antibody, anti-insulin-like growth factor 1 receptor antibody (anti-IGF-1R), anti-Keratin 18 antibody, or one or more antibodies specific to the target of interest.

These and other aspects of the present invention will become apparent from the following description of the preferred embodiment taken in conjunction with the following drawings, although variations and modifications therein may be effected without departing from the spirit and scope of the novel concepts of the invention.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

The following figures form part of the present specification and are included to further demonstrate certain aspects of the invention. The invention may be better understood by reference to one or more of these figures in combination with the detailed description of specific embodiments presented herein. The drawings described below are for illustration purposes only. The drawings are not intended to limit the scope of the present teachings in any way.

FIG. 3B shows the mechanism of loading the nanocomposites with various drugs (in this case doxorubicin), and the quantification of the attachment efficiency by optical spectroscopy. The intensity of one of the drug absorption peaks can be used for this purpose.

DETAILED DESCRIPTION OF THE INVENTION

Figure 1A:
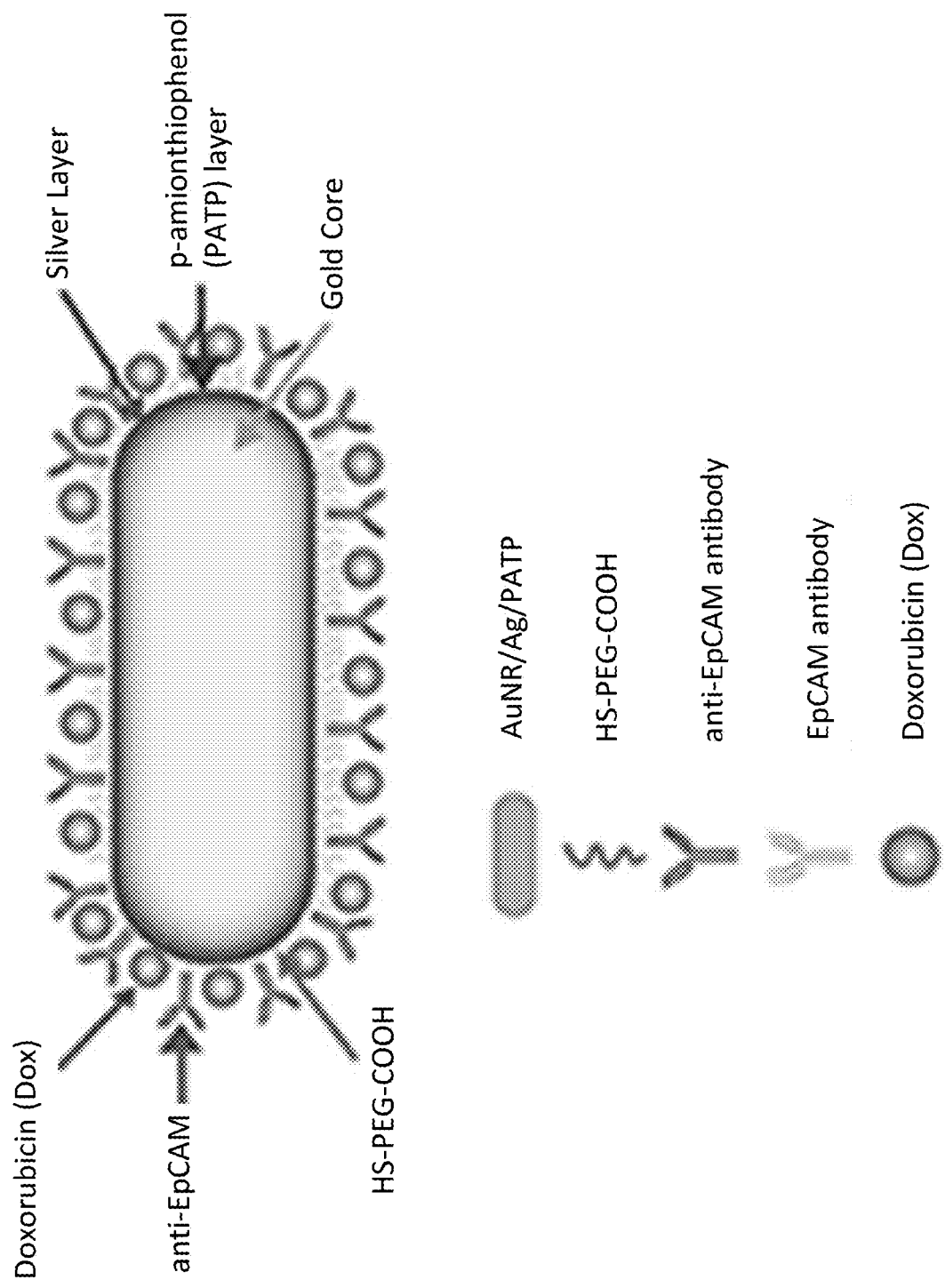
FIG. 1A schematically shows a nanocomposite according to one embodiment of the invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top", may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the invention, and will not be interpreted in an idealized or overly formal sense unless expressly so defined herein.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

As used herein, "around", "about", "substantially" or "approximately" shall generally mean within 20 percent, preferably within 10 percent, and more preferably within 5 percent of a given value or range. Numerical quantities given herein are approximate, meaning that the terms "around", "about", "substantially" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

As used herein, the term "MCF-7" refers to a breast cancer cell line isolated in 1970 from a 69-year-old Caucasian woman. MCF-7 is the acronym of Michigan Cancer Foundation-7, referring to the institute in Detroit where the cell line was established in 1973 by Herbert Soule and co-workers. The Michigan Cancer Foundation is now known as the Barbara Ann Karmanos Cancer Institute. Prior to MCF-7, it was not possible for cancer researchers to obtain a mammary cell line that was capable of living longer than a few months. The patient, whose name, Frances Mallon, is unknown to the vast majority of cancer researchers, died in 1970. Her cells were the source of much of current knowledge about breast cancer. At the time of sampling, she was a nun in the convent of Immaculate Heart of Mary in Monroe, Mich. under the name of Sister Catherine Frances. MCF-7 and two other breast cancer cell lines, named T-47D and MDA-MB -231, account for more than two-thirds of all abstracts reporting studies on mentioned breast cancer cell lines, as concluded from a Medline-based survey.

As used herein, the term "BJ-1 cell line" refers to a normal skin fibroblast cell line, which is available from American Type Culture Collection (ATCC) with ATCC number CRL-2522.

As used herein, the term "circulating tumor cells" or "CTCs" refers to cells that have shed into the vasculature from a primary tumor and circulate in the bloodstream. CTCs thus constitute seeds for subsequent growth of additional tumors (metastasis) in vital distant organs, triggering a mechanism that is responsible for the vast majority of cancer-related deaths.

As used herein, the term "4MBA" refers to 4-mercaptobaezoic acid, PNTP is the abbreviation of p-nitrobenzoic acid, PATP is the abbreviation of p-aminobenzoic acid, 4MSTP is the abbreviation of 4-methylsulfanyl thiophenol, and 4APDS is the abbreviation of 4-aminophenyldisulfide.

As used herein, the term "HS-PEG-COOH and HS-PEG" refer to thiolated polyethylene glycol with or without acid terminal, respectively.

As used herein, the term "phosphate buffered saline" or "PBS" refers to a buffer solution commonly used in biological research. It is a water-based salt solution containing sodium phosphate, sodium chloride and, in some formulations, potassium chloride and potassium phosphate. The osmolarity and ion concentrations of the solutions match those of the human body (isotonic).

As used herein, the term "bovine serum albumin" or "BSA" or "Fraction V" refers to a serum albumin protein derived from cows. It is often used as a protein concentration standard in lab experiments.

As used herein, the term "fetal bovine serum" or "FBS" or "fetal calf serum" refers to the blood fraction remaining after the natural coagulation of blood, followed by centrifugation to remove any remaining red blood cells. Fetal bovine serum comes from the blood drawn from a bovine fetus via a closed system of collection at the slaughterhouse. Fetal bovine serum is the most widely used serum-supplement for the in vitro cell culture of eukaryotic cells. This is due to it having a very low level of antibodies and containing more growth factors, allowing for versatility in many different cell culture applications.

The description will be made as to the embodiments of the present disclosure in conjunction with the accompanying drawings. In accordance with the purposes of this disclosure, as embodied and broadly described herein, this disclosure, in one aspect, relates to multispectral plasmonically active nanostructures for the delivery of multiple drugs to cancer cells and methods of fabricating and using same.

Nanoparticles can be engineered to become a delivery vehicle for cancer chemotherapy. Recently, a promising new system of nanomaterials has been used for specifically targeting and detecting single circulating tumor cells (CTCs) [4] based on plasmonically active nanomaterials constructed using the core-shell approaches. Silver-coated gold nanorods (AuNR/Ag) have unique spectral and surface features that make them a suitable candidate for delivering chemotherapy specifically to tumor cells. These nanosystems have proved to possess multi-color, surface-enhanced Raman spectroscopy (SERS) capabilities, allowing not only rapid detection but also specific targeting of breast cancer MCF-7 cells.

SERS is an intensively investigated approach to study and detect bio-molecular events down to the level of a single molecule [5]. It has been shown that the use of plasmonically active nanosystems can result in their SERS detection and multiplex visualization in complex tissue systems with drastically higher sensitivity (picomolar compared to nanomolar) compared to classical fluorescence of quantum dots [6]. Therefore, significant effort is spent in the construction and testing of SERS agents that can specifically target/detect single cancer cells in circulation, but also deliver drug molecules or other killing agents, while providing a highly specific and intense signal for accurate detection and visualization.

In certain aspects, this invention is based on using plasmonically active silver-decorated gold nanorods (AuNR/Ag) as specific targeting dual drug delivery system. Using coupling reactions, doxorubicin (D1) and anti-EpCAM (Ab1) and Docetaxel (D2) and anti-CD44 (Ab2) antibodies are covalently bound to thiolated polyethylene glycol-coated AuNR/Ag and then used as a vehicle to specifically trace and deliver lethal doses of chemotherapy. This nanorod based system with specific Raman spectroscopic properties could additionally provide unique and strong signals to enable their accurate detection inside cells and further confirm their strong interactions with them. The development of plasmonically active nanodrug concepts with unique signatures could represent a possible approach for the specific targeting and visualization of cells, as well as solid tumors, while delivering anti-cancer molecules for enhanced cancer treatment.

In certain aspects, the invention also relates to a method to deliver to single cancer cell micro- or macro-tumors, a multitude of drug delivery vehicles, each with a different antibody or targeting molecule and each with a different drug. The goal is to synergistically enhance the death rates of the cancer cells by the delivery of a multitude of drugs attached to nanovehicles connected to a multitude of targeting molecules. Additionally, the plasmonic nanorods are decorated with a multitude of Raman scattering molecules that provide multiple signatures for their accurate determination and detection. This method is capable of detecting and quantifying each of the drugs from a multitude of drug cocktails that reach the cancer cells, micro or macro tumors.

Figure 1B:
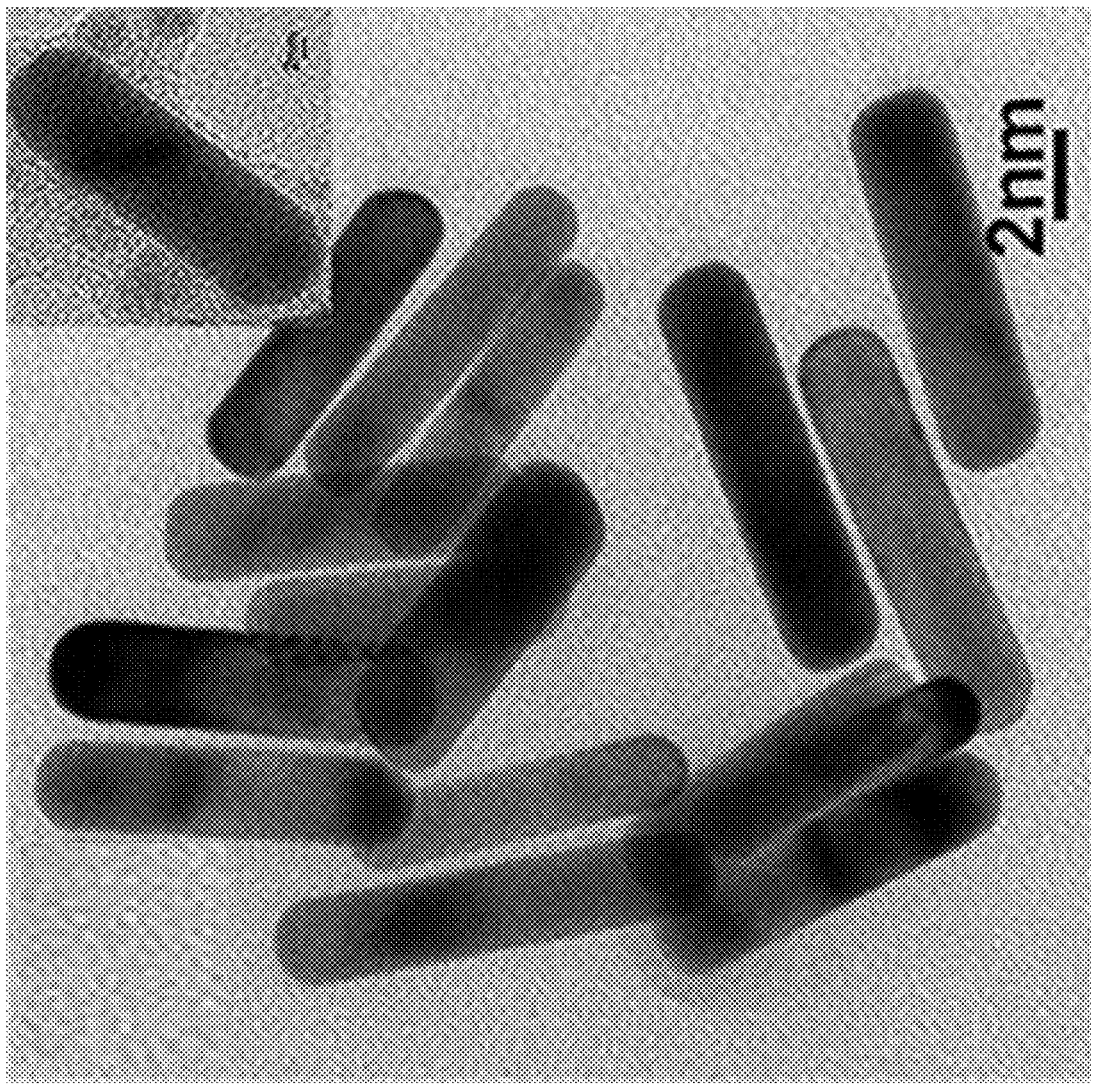
FIG. 1B shows a transmission electron microscopy (TEM) image of nanocomposites according to one embodiment of the invention.

Referring to FIGS. 1A and 1B, and particularly FIG. 1A, a nanocomposite for detection and treatment of a target of interest is shown according to one embodiment of the invention. In exemplary embodiment, the nanocomposite includes one nanostructure having a gold core and a silver layer surrounding the gold core; a reporter, e.g., a p-amionthiophenol (PATP) layer, assembled on the silver layer of the nanostructure; and a layer of a treating agent, e.g., Doxorubicin (Dox), and a targeting agent, e.g., anti-EpCAM, conjugated to the reporter. In addition, the nanocomposite further includes a pegylated layer, e.g., HS-PEG-COOH, formed between the reporter and the layer of the drug and the targeting agent. In certain embodiments, the a pegylated layer may be formed between the silver layer and the reporter (e.g., FIG. 6).

Figure 2:
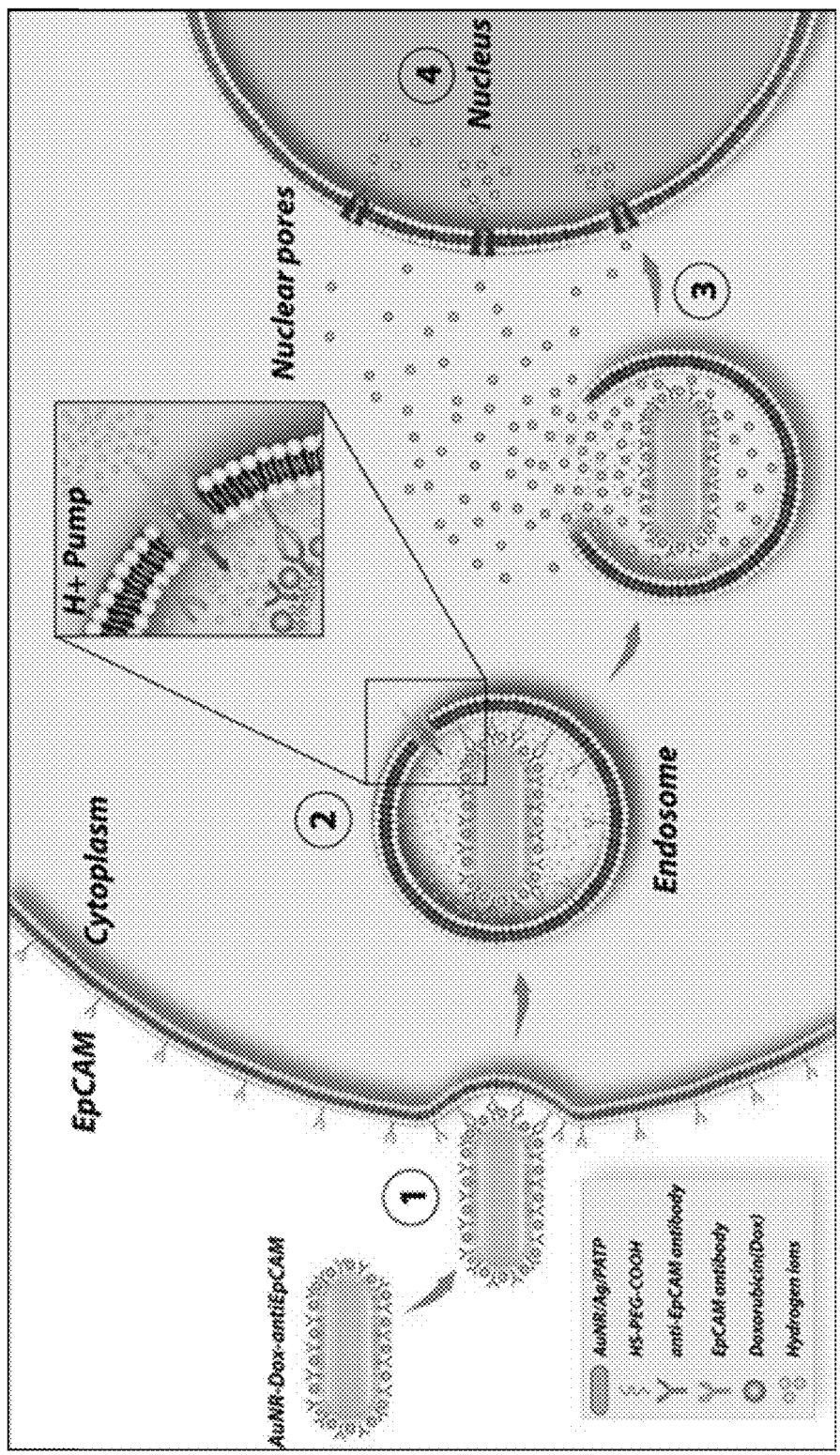
FIG. 2 schematically shows a possible mechanism of killing cancer cells by nanocomposites according to one embodiment of the invention. In this process, the nanomaterials target the surface receptors of the cancer cells and then they get internalized releasing the drugs attached to their surface. The dug is therefore delivered specifically down to single cancer cell level.

As shown in FIG. 2, when in use, the nanocomposite targets the biological target of interest according to the specific targeting agent attached to its surface and releases the treating agent and the nanostructure therein for therapeutic treatment of the target of interest, and the target of interest transmits at least one signature responsive to the reporter for detection of the target of interest. Specifically, we have a carrier (the gold core nanostructure), coated with a silver thin film (0.1-5 nm thickness), which has the role of SERS amplification. This film is coated with a spectroscopically active molecule, which provides the SERS signal. The entire system is coated with a PEG layer, or any other polymer that can provide attachment sites for further functionalization. Also the layer is supposed to keep and shield the silver film from oxidizing and the spectroscopically active molecule from being released or lost. The next step is the functionalization with specific targeting molecules (such as antibodies, fragments of antibodies, proteins, enzymes, growth factors, etc). Additionally the PEG or polymeric layer will be decorated with the drug of choice against the type of biological entity that is targeted.

In certain embodiments, the gold core a gold nanorod (AuNR). The aspect ratio (AR) is defined as the ratio of the length of the AuNR to the diameter of the AuNR. In one embodiment, the AR of the AuNR may be in the range of about 0.3-30, and the length and diameter of the AuNR may be in the range of about 3.6-360 nanometer (nm) and about 1.2-120 nm, respectively. In one embodiment, the AR of the AuNR is in the range of about 1-9. In one embodiment, the preferred AR of the AuNR is in the range of about 2-5. In one embodiment, the preferred AR of the AuNR is in the range of about 2.77-3.23, or about 3±0.23. In one embodiment, the length and diameter of the AuNR may be in the range of about 10-100 nm and about 1-40 nm, respectively. In one embodiment, the particle length and diameter of the AuNR may be approximately 36±0.80 nm and 12±0.41 nm, respectively. In one embodiment, these two dimensions are adequate to form two kinds of surface plasmon modes: a weak one around 520 nm transvers mode, and a very strong longitudinal plasmon around 766 nm. The longitudinal surface plasmon is crucial, and the maximum excitation of this strong surface plasmon mode can be achieved when excited by a Raman excitation laser at about 784 nm. This ensures ultimate sensitivity and very low detection limits when uses SERS for cancer cell detection.

In one embodiment, the silver layer is coated on the AuNR to form a silver coated gold nanorod (AuNR/Ag). In one embodiment, the AuNR and the silver layer have rough surfaces.

In one embodiment, the thickness of the silver layer may be in the range of about 0.2-20 nm. In one embodiment, the thickness of the silver layer is in the range of about 0.5-5 nm. In one embodiment, the thickness of the silver layer is about 1-2 nm. In one embodiment, the thickness of the silver layer is about 1.7 nm. The thin silver layer helps maintain the longitudinal surface plasmon wavelength as close as possible to the excitation laser source (784 nm), in order to achieve the maximum SERS signal. Any thick silver coating will change the surface plasmon significantly.

In one embodiment, the reporter is a Raman reporter molecule layer having Raman reporter molecules. In one embodiment, the Raman reporter molecules are thiolated organic molecules absorbed on the surface of the AuNR/Ag. In one embodiment, the Raman reporter molecule may be at least one of 4-mercaptobenzoic acid (4MBA), p-aminothiophenol (PATP), p-nitrothiophenol (PNTP), 4-(methylsulfanyl) thiophenol (4MSTP), and other molecules with unique Raman spectra and intense Raman peak intensities. In other words, the nanocomposite may have four types: a nanocomposite having a 4MBA reporter layer, a nanocomposite having a PATP reporter layer, a nanocomposite having a PNTP reporter layer, and a nanocomposite having a 4MSTP reporter layer. In certain embodiments, a nanoagent (noncompound) may include all of these four types of nanocomposites. All the SER Raman spectra are obtained through the detection of those Raman reporter molecules. In the exemplary embodiment, the reporter molecule is a Raman reporter molecule.

In certain embodiments, the reporter may include other type of reporter molecules such that the produced nanocomposites may be used together with detecting methods other than SERS, such as MRI, x-ray radiography, CT or IR. In certain embodiments, the reporter molecule is detectable by different methods. In certain embodiments, the report molecules may include one or more fluorescent agents. The one or more fluorescent agents can be quantum dots or fluorescent dyes.

In one embodiment, the pegylated layer is applied to the surface of the SERS reporter molecule coated AuNR/Ag. In some embodiments, the pegylated layer may include thiolated PEG polymers, for example, at least one of HS-PEG, HS-PEG-COOH and HS-PEG-NHx, which are suitable for being used as SERS tags and are non-toxic. Additionally, the thiolated PEG polymers do not displace Raman reporter molecules, which attach to the surface of gold nanoparticles. In certain embodiments, the x in the HS-PEG-NHx is a positive integer. In one embodiment, x is 1 or 2.

In certain embodiments, the pegylated layer includes a mixture of HS-PEG and HS-PEG-COOH, which serves as protective, bio-dispersive and linker to the later conjugated antibodies. In one embodiment, the average molecular weight of the HS-PEG is about 5 kD, and the average molecular weight of the HS-PEG-COOH is about 3 kD. In one embodiment, each nanorod (SERS reporter molecule coated AuNR/Ag) requires about 4,200 molecules to assure complete surface coverage, i.e., each HS-PEG molecule required 0.35 $nm^2$ footprint. The pegylated layer may achieve at least two purposes. First, the pegylated layer protects the nanorods surface and makes the nanocomposite more hydrophilic, and easily disperses the nanocomposite in aqueous medium, for example, biological fluids. Second, the pegylated layer provides a carboxylic terminal on the surface of the SERS reporter molecule coated AuNR/Ag, which is the linker between the SERS reporter molecule coated AuNR/Ag surface and the antibodies that will attached thereon for targeting the target, such as cancer cells.

In certain embodiments, the targeting agent is an antibody. The antibody includes molecules of a type of antibody which specifically targeting certain cancer cell surface antigen. In one embodiment, the antibody is attached covalently to HS-PEG-COOH (—COOH terminal) and plays a role in the specific SERS nanocomposite delivery to the cancer cells.

In one embodiment, the antibody may include molecules of at least one of an anti-EpCAM antibody, an anti-CD44 antibody, an anti-IGF-1R Receptor β antibody, an anti-Keratin 18 antibody, and one or more antibodies specific to the target of interest. In other words, the one or more nanocomposites of the nanoagent may include at least one of the following four types of nanocomposites: the nanocomposite having an anti-EpCAM antibody layer, the nanocomposite having an anti-CD44 antibody layer, the nanocomposite having an anti-IGF-1R Receptor β antibody layer, and the nanocomposite having an anti-keratin 18 antibody layer. In one embodiment, the biocompatible nanoagent having at least one of the four types of nanocomposites may be used for detecting and imaging breast cancer cells, for example, MCF-7, and allow for the capability to distinguish one single cancer cells among normal cells. In one embodiment, the biocompatible nanoagent includes all four types of nanocomposites. In the exemplary embodiments, the targeting agent includes antibodies.

In certain embodiments, the targeting agent may include other type of targeting molecules to specifically binding an object, for example, a ligand that can bind a receptor, or a lectin that can bind a carbohydrate.

In certain embodiments, the treating agent may include one or more molecules of interest attached to the pegylated layer or the targeting agent. In one embodiment, the molecule of interest is a growth factor that induces certain biological functions, including the growth, proliferation of differentiation of cells or organisms. In one embodiment, the molecule of interest is a protein, a drug, or a biological system that induces certain biological functions, the death of cells, tissues, or organisms. The one or more drugs may be anticancer drugs, antibiotics, or antiviral drugs.

In certain aspects of the invention, a method for detection and treatment of a target of interest is provided. The target of interest may include tumor cells or pathogens. In one embodiment, the method includes administering to the target of interest an effective amount of the above nanocomposite, so that the nanocomposite targets to the target of interest according to the targeting agent and releases the treating agent and the nanostructure therein for therapeutic treatment of the target of interest; and measuring the at least one signature transmitted from the target of interest responsive to the reporter to detect the target of interest according to the measured signature. The signature in one embodiment can be the SERS.

In certain aspects of the invention, a nanoagent (or nonaconpound) for detections and treatments of multiple targets of interest is provided, where each target of interest comprises a respective type of tumor cells or pathogens. In one embodiment, the nanoagent comprises multiple types of nanocomposites. Each type of nanocomposites includes at least one nanostructure, each nanostructure having a core and a shell surrounding the core; a respective reporter assembled on the shell of each nanostructure; and a layer of a respective treating agent and a respective targeting agent conjugated to the respective reporter. In one embodiment, each core comprises a nanoparticle including a gold nanorod, and wherein the shell comprises a layer comprising silver nanoparticles.

When in use, each type of nanocomposite targets to a respective target of interest according to the respective targeting agent and releases the respective treating agent and the nanostructure therein for therapeutic treatment of the respective target of interest, and the respective target of interest transmits at least one signature responsive to the respective reporter for detection of the respective target of interest. Accordingly, each of these nanocomposites has a different Raman molecule that provide a different SERS signature. For example, FIG. 4 shows a visualization with multiple SERS signatures of the nanoagent with drugs and antibodies in cancer cells. Specifically, one of the peaks, as presented in FIG. 3A can be used for visualization. The intensity of the peak is measured and mapped over the desired area. Based on this protocol, we can actually visualize and map the presence of the nanocomposites in cells, tissues or other biological environments. We propose the delivery of a "cocktail" of nanocomposite families for a more efficient cancer killing process. Specifically, in our proposed study, we propose to use a multitude of nanocomposite families, each with a different SERS molecule, a different drug and a different targeting molecule (antibody, peptide, etc). In this way, each family of nanocomposite will have a different SERS signature. Moreover, using independent peaks from each of the nanocomposite families, we can visualize each one of them in biological systems. Furthermore, we can quantify the ratio between the presence of various nanocomposite families. By doing this, it is possible to find the ratio of various drugs delivered to the cancer cells and tumors. These plasmonically active nanocomposites can be further activated by laser or electromagnetic excitation for heat generation and a more efficient drug release profile.

In one embodiment, the respective reporter comprises 4-mercaptobenzoic acid (4MBA), p-aminothiophenol (PATP), p-nitrothiophenol (PNTP), 4-(methylsulfanyl) thiophenol (4MSTP), molecules with an unique Raman spectral signature, or a fluorescent agent. Accordingly, the nanoagent may include at least one of the four types of nanocomposites corresponding to four types of reporter molecules. In certain embodiments, the nanoagent may include all four types of nanocomposites. In certain embodiments, the nanoagent may include one, two, three, or more than four types of nanocomposites, and each type of nanocomposite has a special type of reporter molecule. In other embodiments, one type of nanocomposite may include two or more different types of reporter molecules. In certain embodiments, one type of nanocomposite may also include two, three, four or more types of reporter molecules.

In one embodiment, the at least one signature transmitted from the respective target of interest responsive to the respective reporter is detectable by at least one of SERS, MRI, x-ray radiography, CT, and infrared spectroscopy.

In one embodiment, the respective treating agent comprises a drug, a growth factor, a protein, or other biologically active molecules.

In one embodiment, the respective targeting agent comprises anti-epithelial cell adhesion molecule antibody (anti-EpCAM), anti-CD44 antibody, anti-insulin-like growth factor 1 receptor antibody (anti-IGF-1R), anti-Keratin 18 antibody, or one or more antibodies specific to the target of interest.

In one embodiment, each type of nanocomposites further comprises a pegylated layer formed between the respective reporter and the layer of the respective drug and the respective targeting agent, or formed between the shell and the respective reporter.

In one embodiment, the pegylated layer comprises at least one of thiolated polyethylene glycol (HS-PEG), thiolated polyethylene glycol acid (HS-PEG-COOH) and HS-PEG-NHx.

In one embodiment, the respective treating agent and the respective targeting agent are conjugated to the pegylated layer through a carboxylic group of the HS-PEG-COOH or amine group of the HS-PEG-NHx.

In one aspect, the invention relates to a method for detections and treatments of multiple targets of interest, where each target of interest comprises a respective type of tumor cells or pathogens. In one embodiment, the method comprises administering to the multiple targets of interest an effective amount of the above disclosed nanoagent, so that each type of nanocomposite targets to a respective target of interest according to the respective targeting agent and releases the respective treating agent and the nanostructure therein for therapeutic treatment of the respective target of interest; and measuring the at least one signature transmitted from each target of interest responsive to the respective reporter to detect the respective target of interest according to the measured signature.

Figure 5:
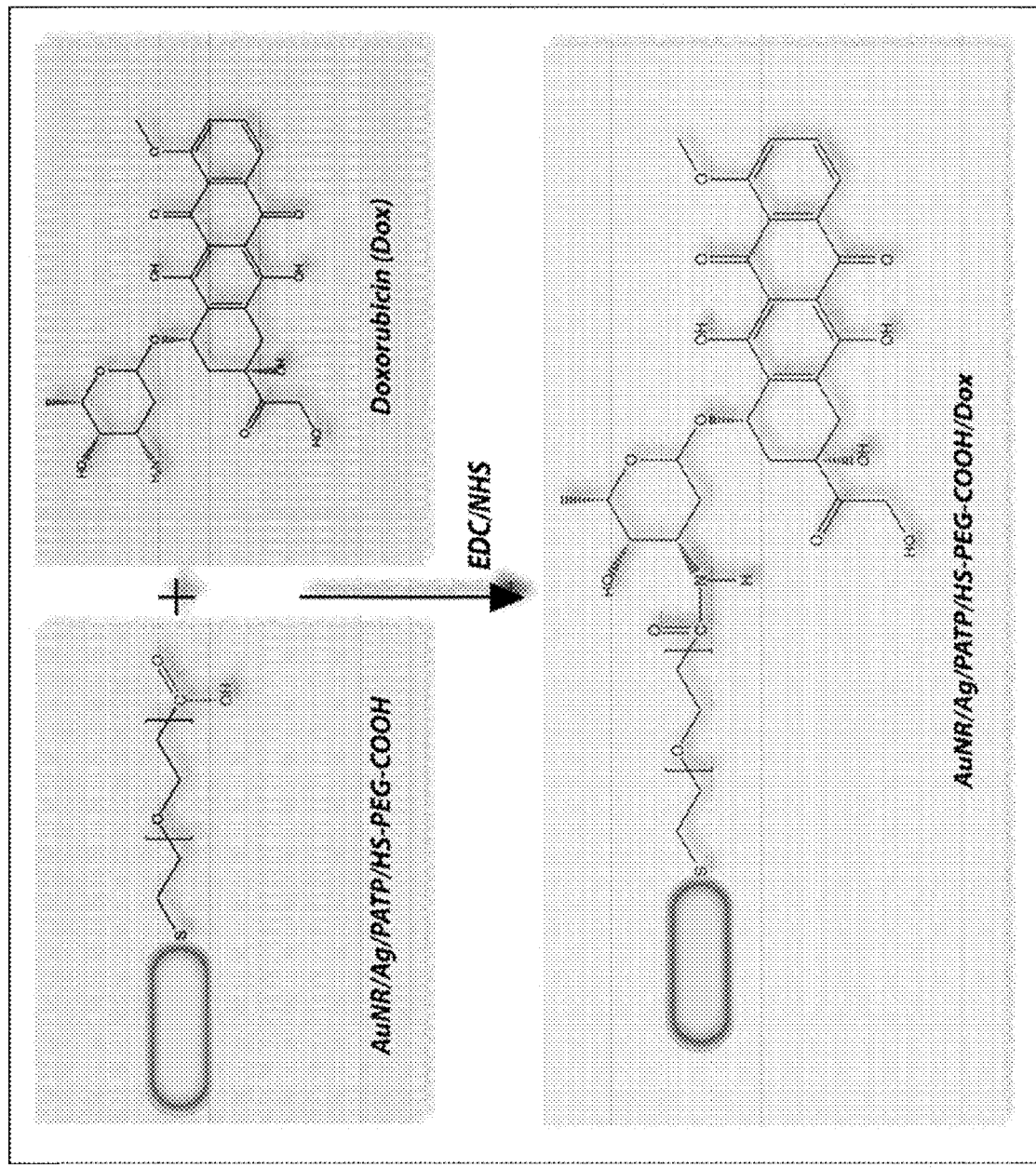
FIG. 5 schematically shows a binding process for attaching drugs and antibodies to the surface of the plasmonically active carriers according to one embodiment of the invention.

In another aspect, the invention relates to a method of making a nanocomposite for detection and treatment of a target of interest. The method includes forming at least one nanostructure, each nanostructure having a core and a shell surrounding the core, e.g., AuNR/Ag. In one embodiment shown in FIG. 5, the method also includes assembling a reporter, e.g., PATP, on the shell of each nanostructure and coating a thiolated PEG layer, e.g., HS-PEG-COOH, on the assembled reporter, e.g., AuNR/Ag/PATP/HS-PEG-COOH. The method further includes conjugating a layer of a treating agent, e.g., Doxorubicin (Dox), to the thiolated PEG layer, e.g., using N-hydroxysuccinimide (NHS) and/or 1N-ethyl-N'-(3-dimethylaminopropyl) carbodiimide hydrochloride (EDC). The conjugated layer may also include a targeting agent.

The reporter is adapted for respectively transmitting at least one signature from the target of interest. The treating agent is adapted for treating the target of interest. The targeting agent is adapted for targeting the nanocomposite to the target of interest.

In certain embodiments, the reporter comprises 4-mercaptobenzoic acid (4MBA), p-aminothiophenol (PATP), p-nitrothiophenol (PNTP), 4-(methylsulfanyl) thiophenol (4MSTP), molecules with an unique Raman spectral signature, or a fluorescent agent.

In certain embodiments, the treating agent comprises a drug, a growth factor, a protein, or other biologically active molecules.

In certain embodiments, the targeting agent comprises anti-epithelial cell adhesion molecule antibody (anti-EpCAM), anti-CD44 antibody, anti-insulin-like growth factor 1 receptor antibody (anti-IGF-1R), anti-Keratin 18 antibody, or one or more antibodies specific to the target of interest.

In one embodiment, the step of assembling the reporter comprises dispersing the at least one nanostructure in distilled water to form a first mixture; dissolving the reporter in ethanol to form a reporter solution; adding the reporter solution to the first mixture and stirring to form a second mixture; and centrifuging the second mixture to form a first precipitate comprising the at least one nanostructure assembled with the reporter.

In one embodiment, the step of coating the thiolated PEG layer on the assembled reporter, includes dispersing the first precipitate in a thiolated polyethylene glycol acid (HS-PEG-COOH) solution and vigorously stirring to form a third mixture; adding thiolated polyethylene glycol (HS-PEG) to the third mixture and keeping it at a temperature for a period of time to form a fourth mixture; and centrifuging the fourth mixture to form a second precipitate, wherein the second precipitate comprises the nanostructure assembled with the reporter coated with the thiolated PEG layer.

In one embodiment, the step of conjugating the layer of the treating agent and the targeting agent to the reporter comprises suspending the second precipitate in a PBS buffer by sonicating to form a suspending mixture; adding NHS and EDC to the suspending mixture and stirring to form a fifth mixture; washing the fifth mixture by centrifuging to obtain a third precipitate; dispensing the third precipitate in the PBS buffer to form a sixth mixture; adding the treating agent and/or the targeting agent to the sixth mixture and mixing thoroughly to form a seventh mixture; and stirring the seventh mixture at a temperature to form the nanocomposite.

Figure 6:
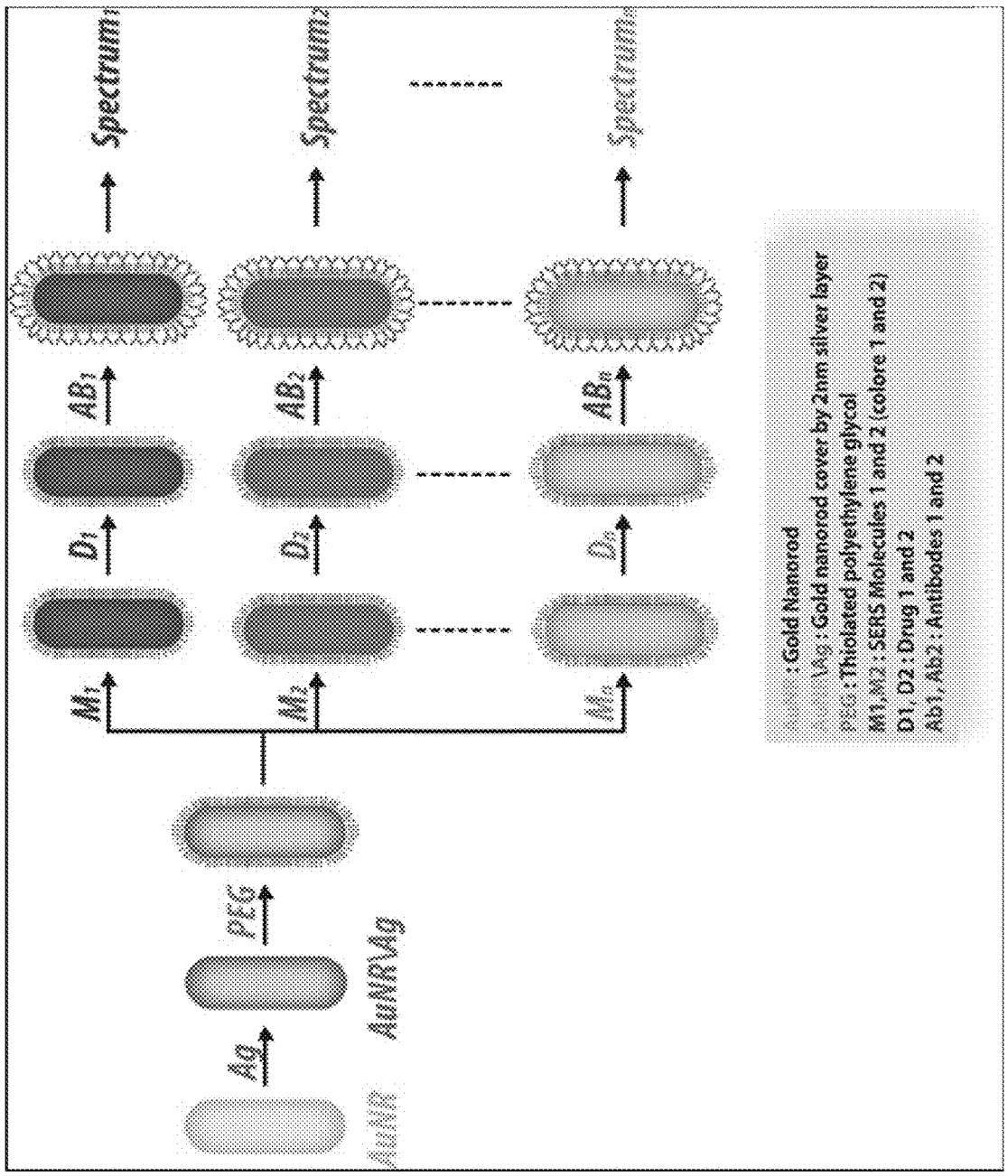
FIG. 6 schematically shows a process for making a nanoagent of plasmonically active nanorods decorated with a multitude of drugs and a multitude of targeting molecules according to one embodiment of the invention. Each of these nanocomposites has a different Raman molecule that provides a different SERS signature.

FIG. 6 shows schematically a process for making a nanoagent of plasmonically active nanorods decorated with a multitude of drugs and a multitude of targeting molecules according to one embodiment of the invention. Each of these nanocomposites has a different Raman molecule that provides a different SERS signature. In certain embodiments, the method for making each type of the nanocomposites is the same as that shown in FIG. 5 above. In other embodiments, the step of coating a thiolated PEG layer is performed prior to the step of assembling a reporter, as shown in FIG. 6.

These and other aspects of the invention are more specifically described below. Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Reagents:

Deionized water (18 Ω/cm) was used in all preparation procedures. The following chemicals were purchased from Sigma-Aldrich: Gold (III) chloride trihydrate (99%), sodium borohydride (99%), L-ascorbic acid (98%), p-aminothiophenol (PATP), Polyvinylpyrrolidone (PVP) (MW about 10,000), N-hydroxysuccinimide (NHS), 1N-ethyl-N'-(3-dimethylaminopropyl) carbodiimide hydrochloride (EDC), Doxorubicin hydrochloride, and HS-PEG-COOH (MW about 3000). Silver nitrate was purchased from Fisher Scientific; exadecyltrimethylammoniumbromide (CTAB 99%) was purchased from MP Biomedicals; SH-PEG (Mw about 5000) was purchased from Nanocs (95%); anti-EpCAM and anti-CD44 were purchased from Cell Signaling at high purities. Doxorubicin and Docetaxel were obtained from Abcam.

Synthesis of Gold nanorods (AuNRs):

AuNRs were prepared according to the silver ion-assisted, seed-mediated method [4, 7]. Specifically, seed solution was prepared as follows: 1 mmol of CTAB solution was added to $2.5 \times 10^{-3}$ mmol Gold chloride solution; next, 0.6 ml of 10 mM sodium borohydride was poured into the solution and stirred for 5 minutes. In order to synthesize the AuNRs solution with an aspect ratio of 3, the following procedure was performed; 1 mmol of CTAB was added to 0.15 ml of 4 mM silver nitrate ($AgNO_3$), then $2.5 \times 10^{-3}$ mmol of $HAuCl_4$ solution were added to the total solution. A small amount of ascorbic acid was added afterward as a reduction agent. 70 μl of 78.8 mM ascorbic acid were added gradually until the mixture became colorless. After that, 12 μl of gold seed solution were added, and the total solution was kept between 27-30° C. for at least forty minutes. Finally, gold nanorods were purified by using 10,000 rpm (30 minutes) centrifugation.

Synthesis of Silver-Decorated Gold Nanorods (AuNR/Ag):

Silver-decorated gold nanorods were synthesized based on an assay described previously [4, 8, 9]. Briefly, 5 ml of 1% Poly(vinylpyrrolidinone) solution were mixed with 5 ml AuNRs in CTAB, then 0.25 ml of 1 mM silver nitrate ($AgNO_3$) solution were added to the total solution and stirred gently. In order to produce a thin layer of metallic silver, 0.1 ml of 100 mM ascorbic acid in basic medium (0.2 ml of 100 mM NaOH) were added and used as a reduction agent. Afterward, decorated nanorods were centrifuged at least twice at 12,000 rpm for 30 minutes to remove any excess chemicals.

Synthesis of SERS Nano-Agents [4]:

Silver-decorated gold nanorods loaded with p-aminothiophenol (PATP) are typically referred to as Surface Enhanced Raman Spectroscopy (SERS) nano-agents [4]. Thiolated small organic molecules (PATP) self-assembled on a silver layer. Approximately 5 μl of 10 mM PATP solution were added to the silver-coated gold nanorods solution and kept at 45° C. for at least 180 minutes.

Afterward, 10,000 rpm centrifugation was performed to remove any excess chemicals.

Conjugation of Doxorubicin (M) and Anti-EpCAM(Ab1) and Docetaxel (D2) and Anti-CD44 (Ab2) with SERS Nano-Agents (Synthesis of D-Ab Conjugates) [4]

SERS nano-agents were re-dispersed in 2 ml of 2 mg/ml carboxyl thiolated polyethylene glycol (HS-PEG-COOH) solution (molecular weight 3000 g/mol), and thiolated PEG solution was prepared in 2 mM solution of sodium chloride. Next, the solution was stirred for 15 minutes. Afterward, 1.8 ml of 2 mg/ml thiolated polyethylene glycol (HS-PEG) were added to the total solution to stabilize the conjugates and kept overnight at 5° C. Excess PEG was removed by centrifugation for 15 minutes at 4000 rpm. NHS/EDC assay [10] was used to conjugate the functionalized PEG coated nanorods with drugs and antibodies. Briefly; 4 ml of purified functionalized nanorods (AuNR/Ag/PATP/PEG) were reacted with antibodies and drugs to obtain AuNR/Ag/PATP/PEG/D-Ab (Nanorod-conjugate). The antibody-tagged, drug-loaded nanorods were purified and re-dispersed in 5 ml of 1×PBS solution and kept at −20° C.

Doxorubicin Loading:

UV-Visible spectra were conducted to calculate the loading percentage of Dox on a certain amount of Nanorod-conjugates. All measurements were conducted at the maximum absorption peak for Dox, 233 nm. According to the standard curve shown in FIG. 3B, the amount of Dox loaded on each Nanorod-conjugates was 4.3%. As part of this process, one or more of the peaks that is specific to each family of nanocomposites can be used to not just visualize them in biological systems, but also to possibly quantify them. Peaks that are not overlapping can be used for the actual analysis. Given the SERS enhancement provided by the Au—Ag structure of the nanocomposites, these peaks are strong enough to where they can be detected easily among various biological systems. FIG. 3B shows the mechanism of loading the nanocomposites with various drugs (in this case doxorubicin), and the quantification of the attachment efficiency by optical spectroscopy. The intensity of one of the drug absorption peaks can be used for this purpose.

Cancer Cells Culture [2, 11]:

Human breast adenocarcinoma (MCF-7) and prostate carcinoma (PC3) cells were purchased from ATCC, then planted according to ATCC protocol in T75 tissue culture flasks at a density of using Dulbecco's modified Eagle medium supported with fetal bovine serum (10%) and penicillin (1%), and streptomycin (500 units/ml)) then incubated at 37° C. in a 5% $CO_2$ atmosphere. Afterward, the cells were sub-cultured by EDTA-trypsinization for further experiments, in which cells were treated with Nanorod-conjugates. The cells were kept in sterilized conditions, and the medium was changed every 48 h.

Cancer Cell Viability Using Nanorod-Conjugates:

MCF7 and PC3 cells' viability was determined after incubation with AuNR-Dox-EpCAM conjugates using WST-1 assay. Briefly, two sets of both cancer cell lines (MCF-7 and PC3) were planted using 96-well plates (density of $10 \times 10^3$) and left to grow for 24 hours. Next, different concentrations (0, 25, 50, 75, 100, 125, and 150 μg/ml) of Nanorod-conjugates (AuNR-Dox-EpCAM) were incubated with both cell lines. After 48 hours of incubation, WST-1 assays were preformed according to Roche® protocol. The assays were repeated in triplicate for statistical analysis; then the $IC_{50}$ values were determined.

Surface-Enhanced Raman Spectroscopy (SERS) Tracing of Nanorod-Conjugates Inside Cancer Cells:

MCF7 and PC3 ($15 \times 10^3$/chamber) were grown in two-sided chamber slides. Within 24 hours of the cells' attachment, 100 μg/mL Nanorod-conjugate were added to each cell line and incubated for 48 hours; subsequently, the cells were fixed using 2% formaldehyde solution then washed 6 times and kept under −20° C.

Characterization of Nanorod-Conjugate (AuNR-D-Ab):

Gold nanorods with specific aspect ratio (width/height being about 3) were prepared according to a seed-mediated method [4, 12]. SERS nano-agents, loaded with drugs and antibodies (Nanorod-conjugates), were prepared according to EDC/NHS coupling reaction using a one-step approach as presented in FIG. 6. Gold nanorods morphology were determined using transmission electron microscopy (TEM) as shown in FIG. 1B. Following this step, nanorods were covered with a thin layer (about 2 nm) of silver [9].

Figure 3A:
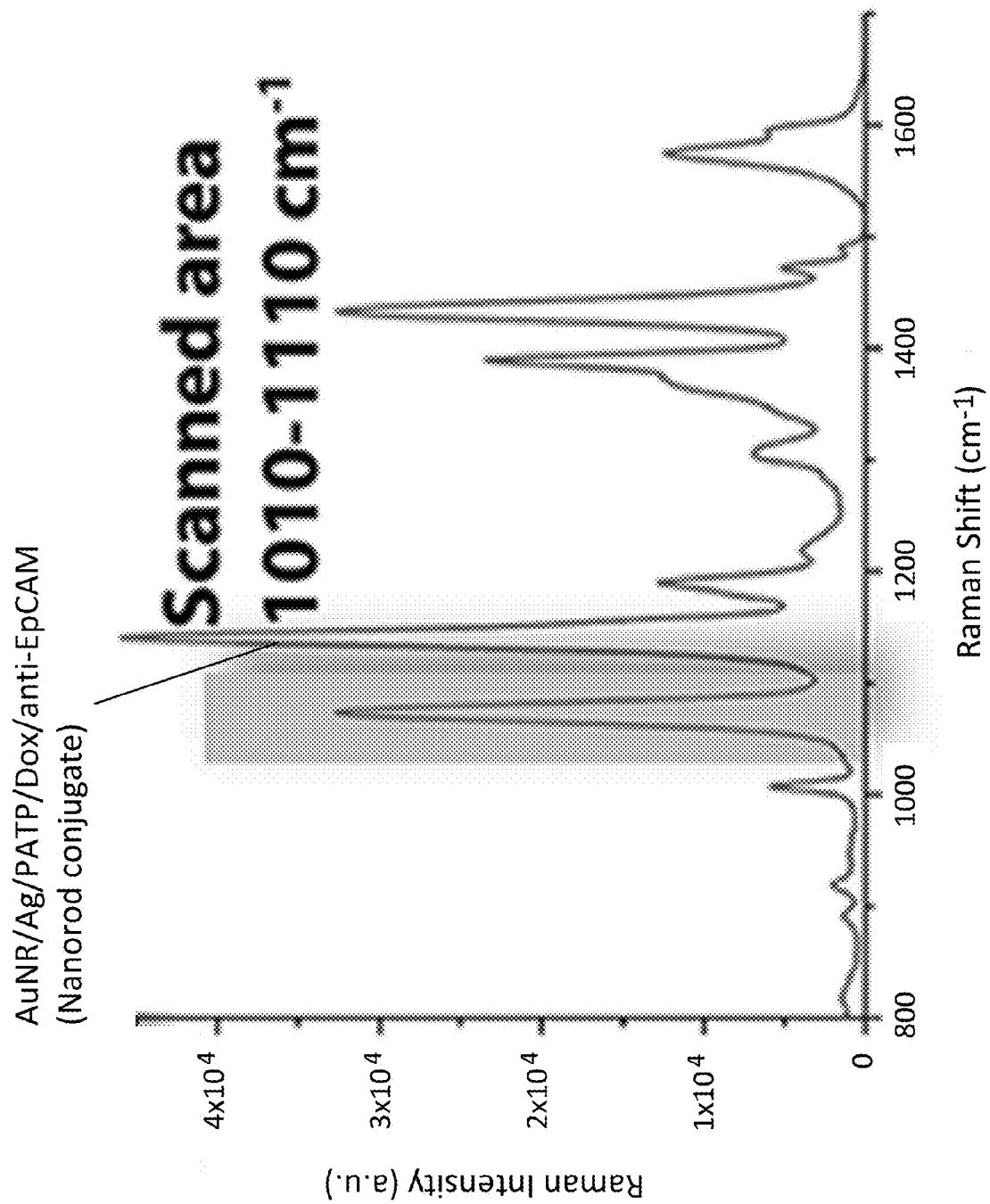
FIGS. 3A and 3B shows Raman spectra in cells and tissues administered with nanocomposites according to one embodiment of the invention. As part of this process, one or more of the peaks that is specific to each family of nanocomposites can be used to not just visualize them in biological systems, but also to possibly quantify them. Peaks that are not overlapping can be used for the actual analysis. Given the SERS enhancement provided by the Au—Ag structure of the nanocomposites, these peaks are strong enough to where they can be detected easily among various biological systems.
Figure 3B:
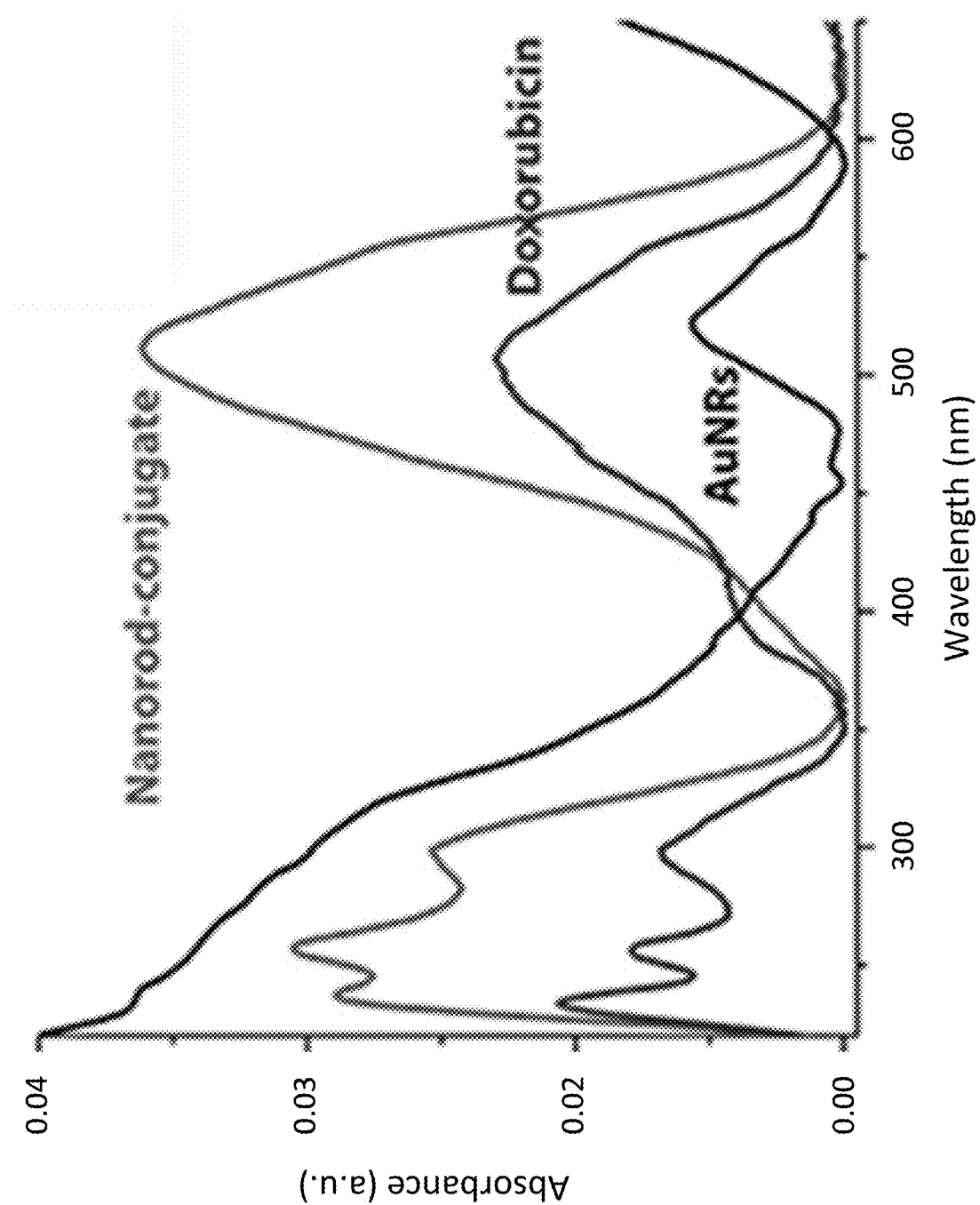
Figure 4:
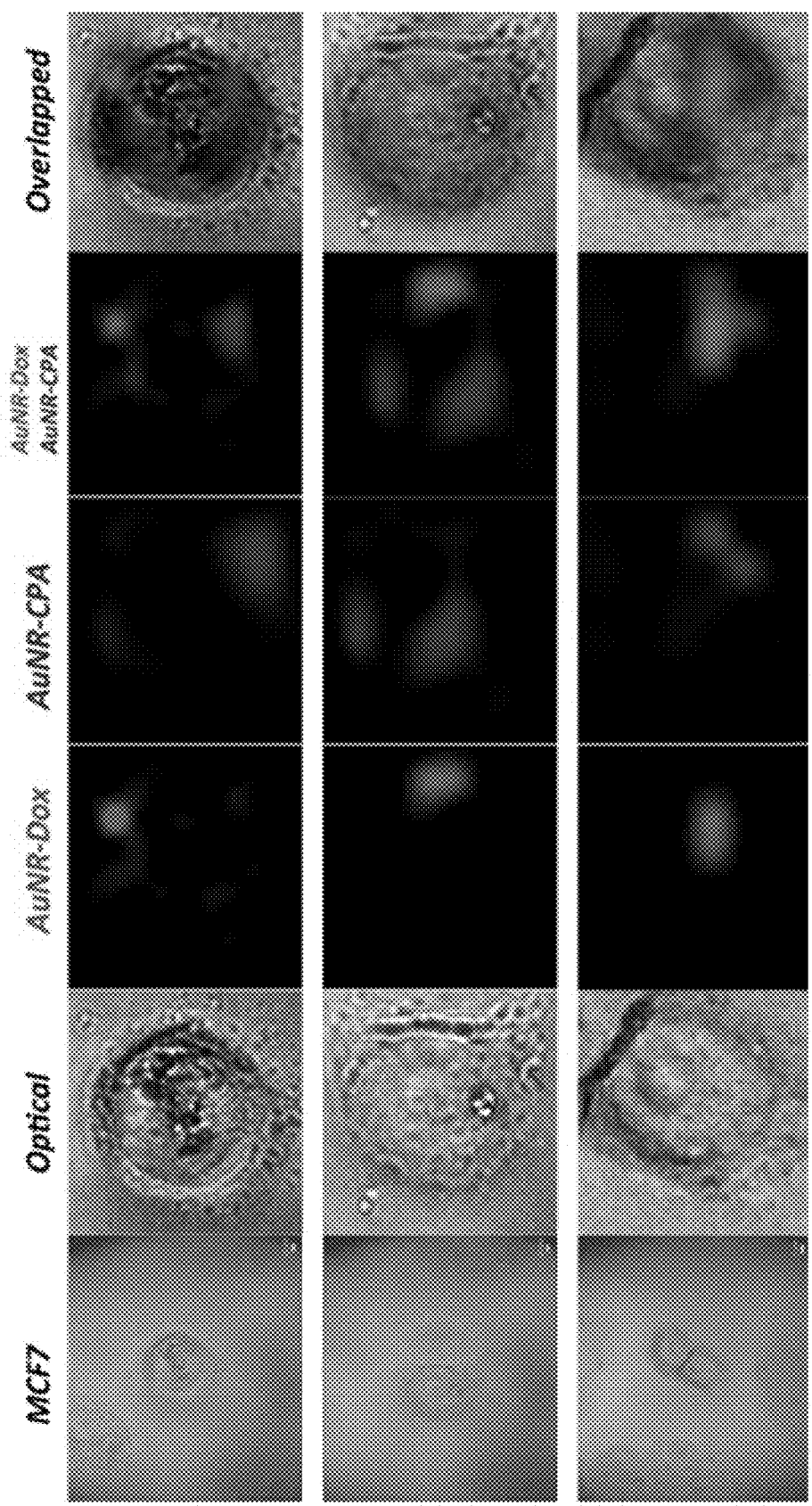
FIG. 4 shows visualization by SERS of the nanocomposites with drugs and antibodies in cancer cells according to one embodiment of the invention. Specifically, one of the peaks, as presented in FIG. 3A can be used for visualization. The intensity of the peak is measured and mapped over the desired area. Based on this protocol, we can actually visualize and map the presence of the nanocomposites in cells, tissues or other biological environments. We propose the delivery of a "cocktail" of nanocomposite families for a more efficient cancer killing process. Specifically, in our proposed study, we propose to use a multitude of nanocomposite families, each with a different SERS molecule, a different drug and a different targeting molecule (antibody, peptide, etc). In this way, each family of nanocomposite will have a different SERS signature. Moreover, using independent peaks from each of the nanocomposite families, we can visualize each one of them in biological systems. Furthermore, we can quantify the ratio between the presence of various nanocomposite families. By doing this, it is possible to find the ratio of various drugs delivered to the cancer cells and tumors. These plasmonically active nanocomposites can be further activated by laser or electromagnetic excitation for heat generation and a more efficient drug release profile.

Synthesis of SERS Nano-Agents:

In order to trace the Nanorod-conjugates inside cells, small organic molecules that scatter light in a specific spectral signature called Raman organic molecules, such as p-aminothiophenol (PATP), were attached to the surface of the nanorods that have a specific Raman signal which can be measured using a Raman spectrophotometer, as shown in FIGS. 3A and 3B.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims as well as the invention including drawings.

LISTING OF REFERENCES

[1]. Cho K, Wang X, Nie S, Chen Z, Shin D M. Therapeutic Nanoparticles for Drug Delivery in Cancer. Clinical Cancer Research. 2008; 14(5):1310-6.

[2]. Saeed L M, Mahmood M, Pyrek S J, Fahmi T, Xu Y, Mustafa T, et al. Single-walled carbon nanotube and graphene nanodelivery of gambogic acid increases its cytotoxicity in breast and pancreatic cancer cells. Journal of Applied Toxicology. 2014:n/a-n/a. doi: 10.1002/jat.3018.

[3]. Mahmood M, Mustafa T, Xu Y, Nima Z, Kannarpady G, Bourdo S, et al. Calcium-channel blocking and nanoparticles-based drug delivery for treatment of drug-resistant human cancers. Therapeutic Delivery. 2014; 5(7):763-80. doi: 10.4155/tde.14.30.

[4]. Nima Z A, Mahmood M, Xu Y, Mustafa T, Watanabe F, Nedosekin D A, et al. Circulating tumor cell identification by functionalized silver-gold nanorods with multicolor, super-enhanced SERS and photothermal resonances. Nat Sci Rep. 2014; 4. doi: 10.1038/srep04752 http://www.nature.com/srep/2014/140509/srep04752/abs/srep04752.html—supplementary information.

[5]. Nima Z A, Biswas A, Bayer I S, Hardcastle F D, Perry D, Ghosh A, et al. Applications of surface-enhanced Raman scattering in advanced bio-medical technologies and diagnostics*. Drug Metabolism Reviews. 2014:1-21. doi: 10.3109/03602532.2013.873451.

[6]. Zavaleta C, Bryan R. Smith, Ian Walton William Doering Glenn Davis Borzoyeh Shojaei Michael J. Natan, Gambhir S S. Multiplexed imaging of surface enhanced Raman scattering nanotags in living mice using noninvasive Raman spectroscopy. PNAS. 2009; 106(32):13511-6.

[7]. Nikoobakht B, Wang J, El-Sayed M A. Surface-enhanced Raman scattering of molecules adsorbed on gold nanorods: off-surface plasmon resonance condition. Chem Phys Lett. 2002; 366(1-2):17-23. doi: http://dx.doi.org/10.1016/S0009-2614(02)01492-6.

[8]. Becker J, Zins I, Jakab A, Khalavka Y, Schubert O, Sonnichsen C. Plasmonic focusing reduces ensemble linewidth of silver-coated gold nanorods. Nano Lett. 2008; 8(6):1719-23. Epub 2008/05/06. doi: 10.1021/n1080720k. PubMed PMID: 18454558.

[9]. Liu M, Guyot-Sionnest P. Synthesis and optical characterization of Au/Ag core/shell nanorods. J Phys Chem B. 2004; 108(19):5882-8. doi: 10.1021/jp037644o.

[10]. Kulin S, Kishore R, Hubbard J B, Helmerson K. Real-Time Measurement of Spontaneous Antigen-Antibody Dissociation. Biophys J. 2002; 83(4):1965-73.

[11]. Nima Z A, Mahmood M W, Karmakar A, Mustafa T, Bourdo S, Xu Y, et al. Single-walled carbon nanotubes as specific targeting and Raman spectroscopic agents for detection and discrimination of single human breast cancer cells. Journal of Biomedical Optics. 2013; 18(5): 055003-. doi: 10.1117/1.jbo.18.5.055003.

[12]. Nikoobakht B, El-Sayed M A. Preparation and growth mechanism of gold nanorods (NRs) using seed-mediated growth method. Chem Mater. 2003; 15(10):1957-62. doi: 10.1021/cm0207321.

What is claimed is:

1. A nanocomposite for detection and treatment of a target of interest, wherein the target of interest comprises tumor cells or pathogens, comprising:
at least one nanostructure, each nanostructure having a core and a shell surrounding the core, wherein each core comprises a nanoparticle including a gold nanorod, and the shell comprises a layer comprising silver nanoparticles;
a reporter assembled on the shell of each nanostructure, wherein the reporter comprises 4-(methylsulfanyl) thiophenol (4MSTP); and
a layer of a treating agent and a targeting agent conjugated to the reporter,
wherein the nanocomposite is configured to target the target of interest according to the targeting agent and release the treating agent and the nanostructure therein for therapeutic treatment of the target of interest, whereby the target of interest transmits at least one signature responsive to the reporter for detection of the target of interest.

2. The nanocomposite of claim 1, wherein the at least one signature transmitted from the target of interest responsive to the reporter is detectable by at least one of surface enhanced Raman spectroscopy (SERS), magnetic resonance imaging (MRI), x-ray radiography, computed tomography (CT), and infrared spectroscopy (IR).

3. The nanocomposite of claim 1, wherein the treating agent comprises a drug, a growth factor, a protein, or other biologically active molecules.

4. The nanocomposite of claim 1, wherein the targeting agent comprises anti-epithelial cell adhesion molecule antibody (anti-EpCAM), anti-CD44 antibody, anti-insulin-like growth factor 1 receptor antibody (anti-IGF-1R), anti-Keratin 18 antibody, or one or more antibodies specific to the target of interest.

5. The nanocomposite of claim 1, further comprising a pegylated layer formed between the reporter and the layer of the treating agent and the targeting agent, or formed between the shell and the reporter.

6. The nanocomposite of claim 5, wherein the pegylated layer comprises at least one of thiolated polyethylene glycol (HS-PEG), thiolated polyethylene glycol acid (HS-PEG-COOH) and HS-PEG-NHx, wherein x is 1 or 2.

7. The nanocomposite of claim 6, wherein the treating agent and the targeting agent are conjugated to the pegylated layer through a carboxylic group of the HS-PEG-COOH or amine group of the HS-PEG-NHx.

8. A nanoagent for detection and treatment of a plurality of targets of interest, the nanoagent comprising a plurality of nanocomposites of claim 1.

9. The nanoagent of claim 8, wherein:
the plurality of nanocomposites comprises a first nanocomposite, a second nanocomposite, a third nanocomposite, and a fourth nanocomposite.

10. The nanoagent of claim 9, wherein:
the targeting agent of the first nanocomposite comprises molecules of anti-epithelial cell adhesion molecule antibody (anti-EpCAM);
the targeting agent of the second nanocomposite comprises molecules of anti-CD44 antibody;
the targeting agent of the third nanocomposite comprises molecules of anti-insulin-like growth factor 1 receptor antibody (anti-IGF-1R); and
the targeting agent of the fourth nanocomposite comprises molecules of anti-Keratin 18 antibody.

11. A nanocomposite for detection and treatment of a target of interest, wherein the target of interest comprises tumor cells or pathogens, comprising:
at least one nanostructure, each nanostructure having a core and a shell surrounding the core;
a reporter assembled on the shell of each nanostructure;
a layer of a treating agent and a targeting agent conjugated to the reporter; and
a pegylated layer formed between the reporter and the layer of the treating agent and the targeting agent, or formed between the shell and the reporter, wherein the pegylated layer comprises HS-PEG-NHx, wherein x is 1 or 2;
wherein the nanocomposite is configured to target the target of interest according to the targeting agent and release the treating agent and the nanostructure therein for therapeutic treatment of the target of interest, whereby the target of interest transmits at least one signature responsive to the reporter for detection of the target of interest.

12. The nanocomposite of claim 11, wherein each core comprises a nanoparticle including a gold nanorod, and wherein the shell comprises a layer comprising silver nanoparticles.

13. The nanocomposite of claim 11, wherein the reporter comprises 4-mercaptobenzoic acid (4MBA), p-aminothiophenol (PATP), p-nitrothiophenol (PNTP), 4-(methylsulfanyl) thiophenol (4MSTP), molecules with an unique Raman spectral signature, or a fluorescent agent.

14. The nanocomposite of claim 11, wherein the at least one signature transmitted from the target of interest responsive to the reporter is detectable by at least one of surface enhanced Raman spectroscopy (SERS), magnetic resonance imaging (MRI), x-ray radiography, computed tomography (CT), and infrared spectroscopy (IR).

15. The nanocomposite of claim 11, wherein the treating agent comprises a drug, a growth factor, a protein, or other biologically active molecules.

16. The nanocomposite of claim 11, wherein the targeting agent comprises anti-epithelial cell adhesion molecule antibody (anti-EpCAM), anti-CD44 antibody, anti-insulin-like growth factor 1 receptor antibody (anti-IGF-1R), anti-Keratin 18 antibody, or one or more antibodies specific to the target of interest.

17. The nanocomposite of claim 11, wherein the treating agent and the targeting agent are conjugated to the pegylated layer through an amine group of the HS-PEG-NHx.

\* \* \* \* \*